United States Patent [19]

Morimoto et al.

[11] Patent Number: 5,389,479
[45] Date of Patent: Feb. 14, 1995

[54] ELECTROPHOTOGRAPHIC PHOTOCONDUCTORS CONTAINING A BIS-ENAMINE COMPOUND

[75] Inventors: Kiyofumi Morimoto, Tenri; Akihiro Kondo, Nara; Satoshi Machino, Joyo; Kazuhiro Emoto, Nagaokakyo; Akiko Masuda, Gose, all of Japan

[73] Assignee: Sharp Kabushiki Kaisha, Osaka, Japan

[21] Appl. No.: 110,929

[22] Filed: Aug. 24, 1993

[30] Foreign Application Priority Data

Sep. 28, 1992 [JP] Japan ................. 4-258141

[51] Int. Cl.$^6$ ............................................. G03G 5/06
[52] U.S. Cl. ........................................ 430/59; 430/71; 430/73; 430/74; 430/75; 430/76
[58] Field of Search ............... 430/59, 71, 73, 74, 430/75, 76

[56] References Cited

U.S. PATENT DOCUMENTS 4,808,505  2/1989  Ueda ........................... 430/59
5,013,623  5/1991  Itoh et al. .................... 430/59

FOREIGN PATENT DOCUMENTS 1-195455 of 1989 Japan.

Primary Examiner—Christopher D. Rodee
Attorney, Agent, or Firm—Nixon & Vanderhye

[57] ABSTRACT

The present invention provides a highly sensitive and highly durable electrophotographic photoconductor providing a conductive support and a photosensitive layer formed thereon, the photosensitive layer comprising a bis-enamine compound of the formula (I):

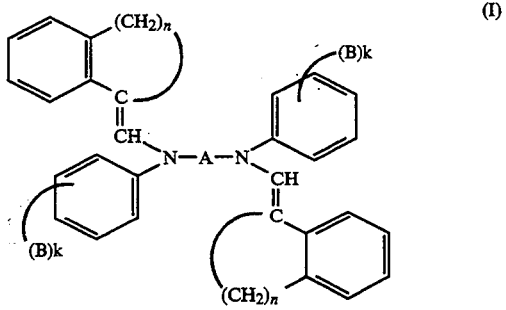

wherein "A" is a $C_{6-12}$ arylene group which may have a substituent, a bivalent heterocyclic reside which may have a substituent, a $C_{2-4}$ lower alkylene group which may have a substituent; "B" is a lower dialkylamino group, a lower alkoxy group, a lower alkyl group, a hydrogen atom or a halogen atom; and k is an integer from 1 to 5 provided that when k is an integer of 2 or more, "B" may be identifcal or different, may together form a ring; and n is an integer from 2 to 4. The electrophotographic photoconductor according to this invention is excellent in stability resisting fluctuations in temperature and humidity, high in electric chargeability, almost free from reduction in photosensitivity in repetitive use and also free from deterioration in image quality such as defection in toner images.

3 Claims, No Drawings ns 5,389,479

ELECTROPHOTOGRAPHIC PHOTOCONDUCTORS CONTAINING A BIS-ENAMINE COMPOUND

BACKGROUND OF THE INVENTION

1. Field of the Invention

The present invention relates to electrophotographic photoconductors. More particularly, it relates to an electrophotographic photoconductor having a conductive support and a photosensitive layer formed thereon, the photosensitive layer containing a bis-enamine compound.

2. Description of the Prior Art

Conventional photosentive layers are utilized inorganic compounds such as selenium, cadmium sulfide, amorphous silicon and zinc oxide. In addition, many studies have been conducted for using organic photoconductive materials as electrophotographic photoconductors.

Basic properties required for electrophotographic photoconductors include the following properties.

(1) A high electrostatic chargeability of electric charge by corona discharge in dark place, (2) Few reduction in electric charge in dark place by corona charge thus obtained, (3) A quick dissipation of an electric charge by light irradiation, (4) Few residual electric charge after light irradiation, (5) A small rise in the residual potential and few reduction in the initial potential through the repetitive use and (6) Few change in the electrophotographic properties and small decrease in the initial potential through repetitive use.

Conventional inorganic materials for electrophotographic photoconductors such as selenium and cadmium sulfide satisfy the above mentioned requirements as a photoconductor in terms of basic properties. However, such materials have drawbacks in the manufacturing process such as, for example, a strong toxicity, difficulty in forming films, little plasticity and a high manufacturing cost. In view of the future prospect, organic materials are more desired than inorganic ones for photoconductors seeing that inorganic materials are restricted in production owing to the depletion of natural resources, and are more likely to cause pollution because of the toxicity thereof.

In view of the above, a brisk research has been performed in recent years on electrophotographic photoconductors formed of organic materials. As a consequence, electrophotographic photoconductors using various organic materials are proposed and some of them are actually manufactured as a product.

Generally speaking, organic materials have several advantages over inorganic materials in that organic materials are more excellent in transparency, lighter in weight, easier to be formed into films than inorganic materials, and that organic materials have both positive and negative chargeability. Such advantages allow easy manufacture of photoconductors formed of organic materials.

Typical organic electrophotographic photoconductors so far proposed include a polyvinylcarbazole and its derivatives. These materials are not sufficient in film-forming properties, plasticity, solubility and adhesiveness. Although a certain degree of improvement has been made to give a photoconductor formed of a polyvinylcarbazole photosensitized with a pyrylium dye (as disclosed in Japanese Patent Publication No. SHO. 48(1973)-25658), and of a polyvinylcarbazole photosensitized with 2,4,7-trinitrofluorenone (as disclosed in U.S. Pat. No. 3,484,237). However, it is still desired to find a photoconductor which satisfies the above-mentioned basic properties as well as mechanical strength and high durability.

In recent years, as disclosed in U.S. Pat. No. 3,791,826, a function-distributed photoconductor is actively proposed wherein two different compounds performs two functions of photoconductive materials such as generation of carriers and transfer of generated carriers. Most of such carrier transferring materials in function-distributed photoconductors are organic compounds having a low molecular weight. Only a limited number of such compounds selected from a wide range thereof can satisfy the basic requirements of photoconductors.

In addition, Japanese Laid-Open Patent No. HEI 1(1989)-195455 discloses that use of a styrene compound containing an enamine group as a carrier transferring material has actualized development of an electrophotographic photoconductor with a considerable sensitivity. Japanese Laid-Open Patent No. HEI 1(1989)-195455 discloses a photoconductor having a conductive substrate and a photosensitive layer formed thereon, the photosensitive layer containing an enamine compound of the general formula (A):

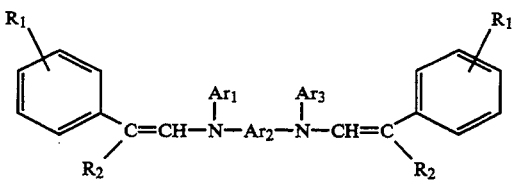

(wherein $R^1$ is a hydrogen, an alkyl group, an alkoxy group, an aralkyl group, a di-substituted amino group, or an aryl group; $R^2$ is hydrogen, an alkyl group, an aryl group that may have a substituent, a condensed polycyclic ring; $Ar_1$, $Ar_2$, and $Ar_3$ represent an alkyl group, an aryl group, a condensed polycyclic group or a heterocyclic group).

However, the above compounds a poor solubility, because they have a high melting point. Coating them will deposit a crystal. Even such compounds having a low melting point did not provide a photoconductor with sufficient properties just because of their inferior sensitivity and the like.

SUMMARY OF THE INVENTION

The present invention provides a highly sensitive and highly durable electrophotographic photoconductor providing a conductive support and a photosensitive layer formed thereon, the photosensitive layer comprising a bis-enamine compound of the formula (I):

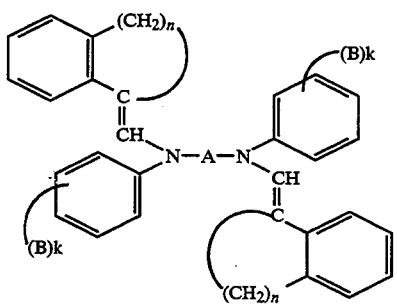

(I)

wherein "A" is a $C_{6-12}$ arylene group which may have a substituent, a bivalent heterocyclic residue which may have a substituent, a $C_{2-4}$ lower alkylene group which may have a substituent; "B" is a lower dialkylamino group, a lower alkoxy group, a lower alkyl group, a hydrogen atom or a halogen atom; and k is an integer from 1 to 5, provided when k is an integer of 2 or more, "B" may be identical or different, or may together form a ring; and n is an integer from 2 to 4.

DESCRIPTION OF THE PREFERRED EMBODIMENTS

The present invention provides an electrophotographic photoconductor having a high sensitivity and a high durability. In particular, the photoconductor of the present invention is excellent in stability resisting changes in temperature and humidity, high chargeability, and free from reduced photosensitivity and deteriorated image quality such as defection of toner images.

In the definition of "A" in the above formula (I), substituents in the "arylene group", the "bivalent heterocyclic residual group" and the "arkylene group" include a $C_{1-3}$ lower alkylene group such as methyl and ethyl, a $C_{1-3}$ alkoxy group like methoxy and ethoxy, a halogen atom such as chlorine or bromine atom. Preferably, each group has one or two of these substituents.

Subsequently, the arylene group in the definition of "A" includes a $C_{6-12}$ aromatic hydrocarbondiyl group. Such hydrocarbondiyl group includes p-phenylene, m-phenylene, p,p'-biphenyldiyl, 1,5-naphthyldiyl and 1,8-naphthyldiyl.

Further, the "bivalent heterocyclic residue" in the definition of "A" includes a six-membered ring residue having one nitrogen atom, a five-membered ring residue having one sulfur atom and a five-membered ring having one sulfur atom and one nitrogen atom. These heterocyclic group may be condensed with a benzene ring. Such example includes 2,6-pyridinediyl, 2,5-benzothiophendiyl, and 2,5-benzothiazolediyl.

In addition, the "$C_{2-4}$ lower alkylene group" in the definition of "A" includes ethylene, trimethylene and tetramethylene.

The symbol "B" includes a hydrogen atom, a lower alkyl group such as methyl and ethyl, a lower alkoxy group such as methoxy and ethoxy, a lower dialkylamino group such as N,N-dimethylamino and N,N-diethylamino, a halogen atom such as chlorine or bromine atom.

Out of the above compounds, those which are excellent in electrophotographic properties, costs, and synthesis include bis-enamine compounds in which "A" is p-phenylene group, m-phenylene group and p,p'-biphenyldiyl group; "B" is a hydrogen atom, a methyl group and a methoxy group; and n is 3.

The bis-enamine compounds (I) of the present invention can be prepared with various methods. Typically, they can be prepared by the following method.

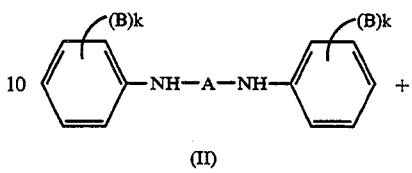

(II)

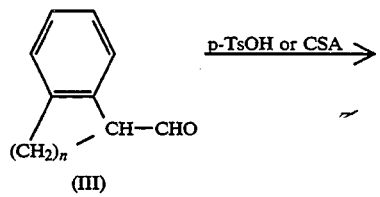

(III)

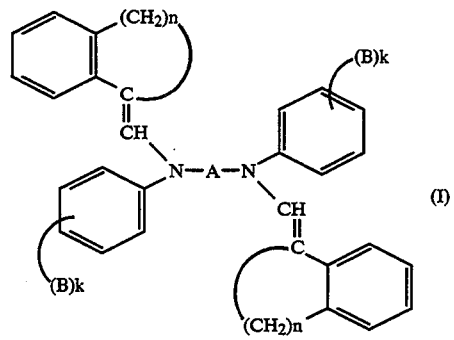

(I)

The reaction of the compound (II) and the compound (III) can be usually conducted in the presence of a condensing agent (e.g., p-toluene sulfonic acid or CSA (DL-10-Camphorsulfonic acid)) in an inert organic solvent (e.g., benzene, toluene, etc.) under heating.

The electrophotographic photoconductor of the present invention can be prepared by containing one or more kinds of the bis-enamine compounds. As a consequence, a highly sensitive and highly durable electrophotpraphic photoconductor is provided.

In some cases, the electrophotographic photoconductor may contain as other carrier transferring materials a styryl compound (such as β-phenyl-(4-dibenzylamino)-stilbene, β-phenyl-[4-(N-ethyl-N-phenylamino)]stilbene, 1,1-bis (4-diethylaminophenyl)-4,4-diphenylbutadiene), triphenylamine compounds (such as 4-methoxy-4'-(p-methoxystyryl) triphenylamine, 4-methoxy-4'-styryltriphenylamine) or hydrazone compounds (such as 4-(dibenzylamino)benzaldehyde-N,N'-diphenylhydrazone, 4-(ethyl-phenylamino)benzaldehyde-N,N-diphenylhydrazone, 3,3-bis[4'-diethylaminophenyl]acrolein-N,N-diphenylhydrazone).

The bis-enamine compound (I) can be used as an electrophotographic photoconductor in various ways. For example, the bis-enamine compound (I) and a dye for sensitizing agent dye, optionally together with an electron-absorbing compound are dispersed or dissolved in a binding resin composition, followed by applying on a conductive substrate. Alternatively, the conductive substrate has a laminate of a carrier generating layer and a carrier transferring layer, in which the carrier generating layer is made of a sensilizing agent dye or a pigment represented by azo pigment or phthalocyanine pigment and the carrier transferring layer is made from a dispersion or solution of the bis-enamine compound (I) (optionally, an antioxidant and electron-absorbing compound added) in the binding resin composition.

Examples of the conductive substrates include a metal drum, a metal plate, paper processed to provide conductivity, a plastic film binding resin or the like.

As resins in the binding resin composition, there may be any one which are used for copying machines and printers, e.g., polystyrene resins, polyvinylacetal resins, polysulfone resins, polycarbonate resins, polyphenylene oxide resins, polyester resins, alkyd resins, polyarylate resins and the like. These resins can be used singly or in a mixture of two or more kinds of these resins. Among them, polystyrene resins, polycarbonate resins, polyacrylate resins, polyphenylene oxide resins have a volumetric resistance of $10^{13}$ Ω or more, which are excellent in film-forming properties and electric properties.

Furthermore, the amount of the binding composition is 0.2 to 20 times by weight to the bis-enamine compound of the present invention, or preferably 0.5 to 5 times by weight. In the range of less than 0.2, the bis-enamine compound may be deposited out from the photoconductor. On the other hand, in the range of 20 times or more, the photosensitivity will be deteriorated.

The use of the bis-enamine compound on the printing plate is desired to use an alkaline binding resin composition, which includes an alkali and may be having an acid group (an acid anhydride group, a carboxy group, a phenolic hydroxyl group, a sulfonic acid group, a sulfonamide group, and a sulfonimide group). Such resins preferably have a high acid value of 100 or more, which can be easily dissolved or swollen in an aqueous or alcoholic alkaline solution. These resins include styrene-maleic anhydride copolymer, vinyl acetate-maleic anhydride copolymer, vinyl acetate-crotonic acid copolymer, methacrylic acid-methacrylate copolymer, phenol resin, and methacrylic acid-styrene-metacrylate copolymer. Besides, the ratio of these resins to be added to the photoconductive organic material is approximately equal to that of the photoconductor used in copying machines.

The sensitizing dyes include triphenylmethane dye such as Methyl Violet, Crystal Violet, Night Blue and Victoria Blue, acridine dye such as Erythrocin, Rhodamine B, Rhodamine 3R, Acridine Orange and Flapeocin; thiazine dyes such as Methylene Blue and Methylene Green; oxadine dyes such as Capri Blue and Meldola's Blue; other dyes such as cyanine dyes, styryl dyes, pyrilium salt and thiopyrilium salt dyes.

Pigments which generates charge carriers at an extremely high efficiency with light absorption in the carrier generating layer include phthalocyanine pigments such as various metal phthalocyanines, nonmetallic phthalocyanines and halogenated nonmetallic phthalocyanines, perylene pigments such as peryleneimide and perylenic anhydride, azo pigments such as bis-azo pigments and tris-azo pigments, quinacridone pigments and anthraquinone pigments.

Especially preferred pigments which generate charge carriers are non-metallic phthalocyanine pigments, bis-azo pigments containing fluorenylidene or fluorenone group, bis-azo pigments containing aromatic amine moiety or tris-azo pigments, which can provide high sensitivity.

Furthermore, the above dye may also be used as a material for generating charge carriers. Those dyes may be used independently. In most cases, those dyes are used in mixture with pigments to separate charge carriers at a high efficiency. In addition to the above spectral sensitizers, various chemical substances are required to inhibit sensitivity deterioration, reduction in charged electric potential and an increase in residual electric potential through repetitive use.

Such chemical materials include an electron attracting compound such as tribenzylamine, tetrabenzyl-p-xylenediamine, 1-chloroanthraquinone, benzoquinone, 2,3-dichloronaphthoquinone, naphthoquinone, 4,4'-dinitrobenzophenone, 4,4'-dichlorobenzophenone, 4-nitrobenzophenone, 4-nitrobenzalmalondinitrile, α-cyano-β-(p-cyanophenyl)acrylate ethyl, 9-anthracenylmethyl malondinitrile, 1-cyano-1-(p-nitrophenyl)-2-(p-chlorophenyl)ethylene and 2,7-dinitro- fluorenone.

In addition, the photoconductor may contain an antioxidant, anticurl agents and leveling agents as additives if required.

The bis-enamine compound of the present invention is dissolved or scattered in an appropriate solvent along with the above additives depending upon the form of the photoconductor, which is followed by coating a coating agent on the aforementioned conductive support and drying it to manufacture the photoconductor of the present invention.

Solvents for coating include aromatic hydrocarbons such as benzene, toluene, xylene and monochlorobenzene, halogenated hydrocarbons such as methylene chloride and dichloroethane, dioxane, dimethoxy methyl ether and dimethylformamide. Such solvents may be used singly, or in mixture of the two different kinds. If required, they may be used by adding alcohols, and solvents like acetonitrile, methyl ethyl ketone, etc.

EXAMPLES

The present invention will be further illustrated with respect to the following examples, which are given only for exemplifying purposes, and cannot be construed as limiting the scope of the invention itself.

First, examples of synthesis of the compounds used in the working examples of the present invention will be given as hereinafter.

Synthetic Example 1

(Exemplified Compound No. 14)

N,N'-diphenylbenzidine and two equivalent 1,2,3,4-tetrahydro-1-formylnaphthalene were heated in toluene at 120° C. in the presence of DL-camphor-sulfonic acid catalyst to be subjected to dehydration condensation to give Exemplified compound No. 14 (melting point 196°-199° C.). Incidentally, the exemplified compound was recrystallized in ethyl acetate.

Subsequently, bis-enamine compound synthesized in the same manner as the above exemplified example is exemplified in Table 1 through 4.

TABLE 1

| compound No. | A | (B)$_K$ | n |
|---|---|---|---|
| 1 | 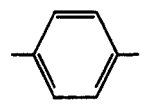 | H | 3 |

TABLE 1-continued

| compound No. | A | (B)$_K$ | n |
|---|---|---|---|
| 2 | phenylene | 4-CH$_3$ | 3 |
| 3 | phenylene | 4-OCH$_3$ | 3 |
| 4 | phenylene | 4-N(CH$_3$)$_2$ | 3 |
| 5 | phenylene | 3-CH$_3$ | 3 |
| 6 | phenylene | 3-OCH$_3$ | 3 |
| 7 | m-phenylene | H | 3 |
| 8 | m-phenylene | 4-CH$_3$ | 3 |
| 9 | m-phenylene | 4-OCH$_3$ | 3 |

TABLE 2

| No. | A | (B)$_K$ | n |
|---|---|---|---|
| 10 | m-phenylene | 3-CH$_3$ | 3 |
| 11 | m-phenylene | 3-OCH$_3$ | 3 |
| 12 | m-phenylene | 3-OCH$_3$, 5-OCH$_3$ | 3 |
| 13 | m-phenylene | 3-CH$_3$, 5-CH$_3$ | 3 |
| 14 | biphenylene | H | 3 |
| 15 | biphenylene | 3-CH$_3$ | 3 |
| 16 | biphenylene | 4-CH$_3$ | 3 |
| 17 | biphenylene | 3-CH$_3$, 5-CH$_3$ | 3 |
| 18 | biphenylene | 3-OCH$_3$ | 3 |

TABLE 3

| No. | A | (B)$_K$ | n |
|---|---|---|---|
| 19 | biphenylene | 4-OCH$_3$ | 3 |
| 20 | biphenylene | 4-N(C$_2$H$_5$)$_2$ | 3 |
| 21 | dichlorobiphenylene | H | 3 |
| 22 | biphenylene | H | 2 |
| 23 | biphenylene | H | 4 |
| 24 | naphthylene | H | 3 |
| 25 | naphthylene | 4-CH$_3$ | 3 |

TABLE 3-continued

| No. | A | (B)$_K$ | n |
|---|---|---|---|
| 26 | [1,5-disubstituted naphthalene] | H | 3 |
| 27 | [1,8-disubstituted naphthalene] | 3-CH$_3$ | 3 |

TABLE 4

| No. | A | (B)$_K$ | n |
|---|---|---|---|
| 28 | [2,6-disubstituted pyridine] | H | 3 |
| 29 | [2,6-disubstituted pyridine] | 3-CH$_3$ | 3 |
| 30 | [2,6-disubstituted pyridine] | 3-OCH$_3$ | 3 |
| 31 | [4-methyl-2,6-disubstituted pyridine] | H | 3 |
| 32 | [disubstituted benzothiophene] | H | 2 |
| 33 | [disubstituted benzothiophene] | H | 3 |
| 34 | [disubstituted benzothiophene] | H | 4 |
| 35 | —CH$_2$CH$_2$— | H | 2 |
| 36 | —CH$_2$CH$_2$— | H | 3 |

Examples 1-5

A bis-azo dye of the following formula was added in the same weight as phenoxy resin (PKHH: manufactured by Union Carbide) to 1% solution of THF in which phenoxy resin was dissolved, dispersed for about 2 hours with a glass beads having a diameter of 1.5 mm in a paint conditioner (manufactured by Red Level Inc.).

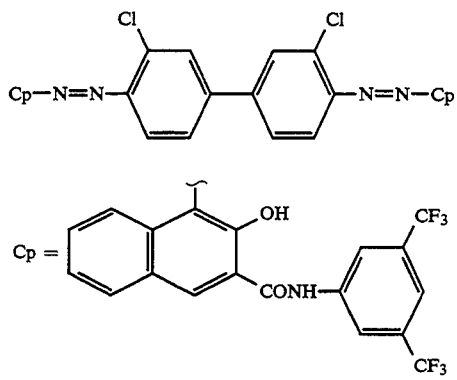

The resulting dispersant was used as a material for coating and drying an aluminum-vapor-deposited polyester film support with a thickness of 80 μm with the doctor blade process. The thickness of the dispersed dye layer after the coating and drying process was 0.2 μm. On this resulting dye layer (carrier generating layer) was coated 15% solution in which 1 g of the Exemplified compound No. 5, No. 6, No. 7, No. 14 or No. 15 and 1.2 g of polyarylate (U-100; manufactured by Unitika,ltd.) were dissolved in methylene chloride with the squeezing doctor process to manufacture a resin-biz-enamine compound solid solution phase (carrier transferring layer) of 25 μm in thickness after the drying process.

The laminated electrophotographic photoconductor thus manufactured was evaluated on electrophotographic properties with a device for electrostatic recording paper experimenting device (SP-428; manufactured by Kawaguchi Electric Co, Ltd). The measuring conditions were: applied voltage of −6 kV, static No. 3. The exposure amount $E_{100}$ (lux-second) and the initial potential Vo (-volts) required for reducing −700 V to −100 V by white light illumination was measured. Table 6 shows the result of the measurements.

Furthermore, the above device-for-electrostatic recording paper experimenting device was used to measure the initial potential (-volts) and the exposure amount $E_{100}$ (lux-second) after conducting 10000 cycles of electrostatic charge and discharge (discharge light; illuminating white light of 40 lux for one second), thereby examining changes in $V_0$ and $E_{100}$. Table 5 shows the result of the measurements.

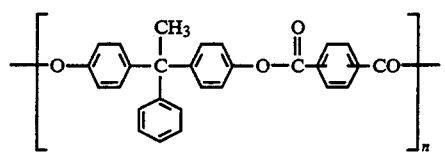

TABLE 5

| | | 1 cycle | | 10000 cycles | |
|---|---|---|---|---|---|
| photoconductor | exemplified bis-enamine compound | $V_0$ (−vol) | $E_{100}$ (lux · sec) | $V_0$ (−vol) | $E_{100}$ (lux · sec) |
| Example 1 | comp No. 5 | 800 | 1.9 | 790 | 2.0 |
| Example 2 | comp No. 6 | 820 | 1.8 | 810 | 1.8 |
| Example 3 | comp No. 7 | 800 | 2.0 | 780 | 2.1 |
| Example 4 | comp No. 14 | 810 | 2.1 | 790 | 2.2 |
| Example 5 | comp No. 15 | 840 | 1.7 | 830 | 1.8 |

Table 5 shows that the bis-enamine compound of the present invention is favorable in terms of sensitivity and repetitive properties.

Example 6

Nonmetallic phthalocyanine of type X (Fast Gemblue 8120; manufactured by Dainippon Ink and Chemicals, Inc.) (0.4 g) was added to 30 ml of 0.3 g of vinyl chloride-vinyl acetate copolymer resin (Eslex M; manufactured by Sekisui Chemical Co.,Ltd.) in ethyl acetate. The mixutre was dispersed for about 20 minutes in a paint conditioner. The resulting dispersion was coated by a doctor blade method on aluminum vapor deposited polyester film coated with aluminum by evaporation, following by drying. Thus, on this carrier generating layer was formed to a dried thickness of 0.4 µm.

On this carrier generating layer was laminated a polyacrylate layer containing 50% weight ratio of Exemplified compound No. 13, to manufacture a photoconductor comprising two-layers.

The energy ($E_{50}$) and the initial potential $V_0$ (-volts) required for reducing the potential level of the photoconductor was determined from the spectrum having a wavelength of 780 nm. The investigation test shows the following result; $V_0=860$(-volts), $E_{50}=2.6$(erg/cm$^2$). Consequently, a highly sensitive photoconductor with high chargeability was obtained.

In addition, a laser printer (WD-580P) manufactured by Sharp Kabushiki Kaisha was reformed so that the photoconductor was laminated on the drum to investigate a reduction in the initial potential and a reduction in the sensitivity. The result of the investigation after 10000 tests shows $V_0=850$ (-volts), $E_{50}=2.6$ (erg/cm$^2$), which are almost equal to the counterparts in the first test.

Examples 7-10

A support whose alumina substrate surface was processed with alumite (alumite layer; 7 µm) was coated with a solution formulated by dissolving in methylene chloride a bis-enamine compound (1 g) of the present invention, polyacrylate resin (1.1 g), N,N-3,5-xylyl-3,4-xylyl-3,4,9,10-perylenetetracarboxylimide (0.15 g) and an ultraviolet absorbent (0.15 g) by an applicator to a single layer photoconductor to a dried thickness of 20 µm.

The photoconductor thus manufactured was subjected to a measurement of electrophotographic properties with an electrostatic recording paper test device. the measuring conditions were determined as; applied voltage of +5.5 kV, static No. 3. The exposure amount $E_{100}$ (lux·sec) required for reducing +700 V to +100 V by white light illumination was measured and the result of the measurement was shown in Table 6. In addition, the photoconductor of the present invention was subjected to 10000 cycles aging tests without feeding paper into the device in which the sensitivity ($E_{100}$) and degree of deterioration were measured. The result of the measurements are shown in Table 6.

TABLE 6

| photoconductor | exemplified bis-enamine compound | $E_{100}$ (lux · sec) 1 cycle | $E_{100}$ (lux · sec) 10000 cycles |
| --- | --- | --- | --- |
| Example 7 | comp No. 1 | 2.5 | 2.6 |
| Example 8 | comp No. 11 | 2.7 | 2.8 |
| Example 9 | comp No. 16 | 2.3 | 2.5 |
| Example 10 | comp No. 19 | 2.6 | 2.7 |

Comparative Example

In accordance with the present invention, as a material for synthesizing a bis-enamine compound a cyclic aldehyde compound is used. Here, as described in Japanese Laid-Open Patent No. HEI 1-195455, a non-cyclic alhedyde compound was used to synthesize an enamine compound. The enamine compound thus prepared generally has a poor solubility, because they have a high melting point. Coating the enamine compound will deposit a crystal. Even when the enamine compound has a low melting point, it has a poor sensitivity. As a consequence such compound cannot provide a photoconductor with an excellent properties.

For example, a compound having a diphenyl structure has a high melting point of 211° to 213° C. Thus, it has a very poor solubility. Coating the compound will deposit a crystal, which makes it very difficult to use it as a photoconductor.

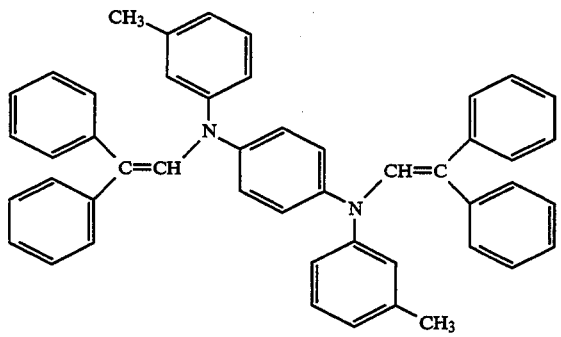

In addition, a compound having a structure of a phenylmethyl moiety shown hereinbelow has a melting point of 132° C., which is lower than the above. It has an exposure quantity of $E_{100}$ of 2.5 (lux·sec) which means that the compound is inferior to the above in sensitivity.

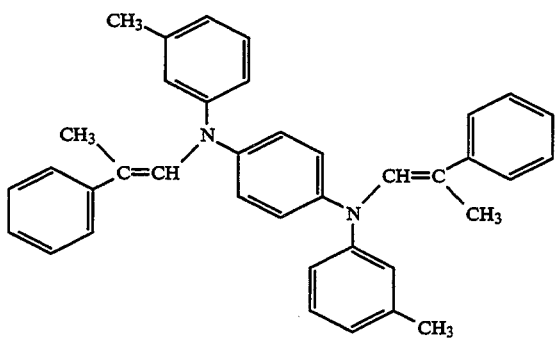

On the other hand, Exemplified compound No. 5 of the present invention shown hereinbelow has a low melting point of 105° C. and a favorable solubility. It further has an exposure quantity $E_{100}$ of 1.9 (lux·sec), thereby providing a sufficient sensitivity to be used as a photoconductor.

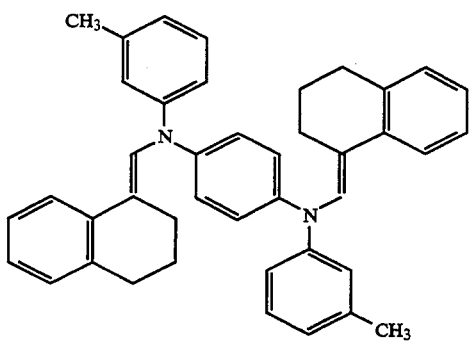

The above examples show that the photoconductor using the bis-enamine compound of the present invention has a favorable repetitive properties having an excellent sensitivity in positive charge.

What is claimed is:

1. An electrophotographic photoconductor providing a conductive substrate and a photosensitive layer formed thereon, said photosensitive layer comprising a bis-enamine compound of the formula (I):

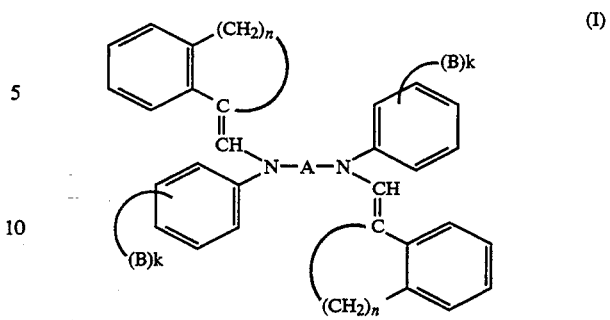

wherein A is a $C_{6-12}$ arylene group which may have a substituent, a bivalent heterocyclic residue which may have a substituent, or a $C_{2-4}$ lower alkylene group which may have a substituent; "B" is a lower dialkylamino group, a lower alkoxy group, a lower alkyl group, a hydrogen atom or a halogen atom; and "k" is an integer from 1 to 5 provided that when k is an integer of 2 or more, the Bs, which may be identical or different, may together form a ring; and n is an integer from 2 to 4.

2. The electrophotographic photoconductor of claim 1 wherein said photosensitive layer comprises a carrier transferring material and a carrier generating material, said carrier transferring material being a bis-enamine compound of the formula (I).

3. The electrophotographic photoconductor of claim 1 wherein said photoconductive layer comprises a laminate member having of a carrier generating layer containing a carrier generating material and a carrier transferring layer containing a carrier transferring material, said carrier transferring material containing a bis-enamine compound of the general formula (I).

* * * * *